(12) United States Patent
Chen et al.

(10) Patent No.: US 10,722,209 B2
(45) Date of Patent: Jul. 28, 2020

(54) ULTRASOUND SYSTEM AND METHOD OF VESSEL IDENTIFICATION

(71) Applicant: KONINKLIJKE PHILIPS N. V., Eindhoven (NL)

(72) Inventors: Jiangang Chen, Minhang (CN); Balasundar Iyyavu Raju, North Andover, MA (US); Evgeniy Leyvi, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 128 days.

(21) Appl. No.: 15/316,535

(22) PCT Filed: Mar. 31, 2016

(86) PCT No.: PCT/EP2016/056984
§ 371 (c)(1),
(2) Date: Dec. 6, 2016

(87) PCT Pub. No.: WO2016/156446
PCT Pub. Date: Oct. 6, 2016

(65) Prior Publication Data
US 2018/0014810 A1 Jan. 18, 2018

(30) Foreign Application Priority Data

Apr. 3, 2015 (WO) ................ PCT/CN2015/075831
Jun. 4, 2015 (EP) ..................................... 15170630

(51) Int. Cl.
*A61B 8/06* (2006.01)
*A61B 8/08* (2006.01)
(Continued)

(52) U.S. Cl.
CPC ................ *A61B 8/06* (2013.01); *A61B 8/085* (2013.01); *A61B 8/0891* (2013.01); *A61B 8/14* (2013.01);
(Continued)

(58) Field of Classification Search
CPC .. A61B 8/00; A61B 8/06; A61B 8/523; A61B 8/4494; A61B 8/085; A61B 8/5284;
(Continued)

(56) References Cited

U.S. PATENT DOCUMENTS 6,068,598 A * 5/2000 Pan .......................... A61B 8/06
600/453
6,071,242 A * 6/2000 Lin .......................... A61B 8/06
600/456
(Continued)

FOREIGN PATENT DOCUMENTS

CN 103445808 A 12/2013
JP 2007275457 A 10/2007
(Continued)

OTHER PUBLICATIONS

Wallace, David J., Michael Allison, and Michael B. Stone. "Inferior vena cava percentage collapse during respiration is affected by the sampling location: an ultrasound study in healthy volunteers." Academic Emergency Medicine 17.1 (2010): 96-99.).*
(Continued)

*Primary Examiner* — Luther Behringer
*Assistant Examiner* — Sean D Mattson

(57) ABSTRACT

An ultrasound system for identifying a vessel of a subject comprises: an ultrasound probe configured to simultaneously acquire a sequence of ultrasound blood flow data frames (such as a sequence of ultrasound Doppler data frames) and a sequence of ultrasound B-mode data frames of a region of interest including the vessel over a predeter-
(Continued)

mined time period; a blood flow region selecting unit configured to select a blood flow region in the sequence of blood flow data frames; and a vessel segmenting unit configured to segment the vessel in at least one frame of the sequence of ultrasound B-mode data frames based on the selected blood flow region. Since there is no need to manually place any seed point for vessel segmentation any more, the user dependency is reduced and a fast measurement is made possible.

17 Claims, 10 Drawing Sheets

(51) Int. Cl.
    *A61B 8/00*     (2006.01)
    *A61B 8/14*     (2006.01)
    *G01B 17/00*     (2006.01)
    *G01N 29/24*     (2006.01)

(52) U.S. Cl.
    CPC ............ *A61B 8/4494* (2013.01); *A61B 8/469* (2013.01); *A61B 8/481* (2013.01); *A61B 8/488* (2013.01); *A61B 8/523* (2013.01); *A61B 8/5223* (2013.01); *A61B 8/5246* (2013.01); *A61B 8/5284* (2013.01); *G01B 17/00* (2013.01); *G01N 29/2406* (2013.01); *G01N 29/2437* (2013.01); *G01N 2291/017* (2013.01); *G01N 2291/02466* (2013.01)

(58) Field of Classification Search
    CPC ....... A61B 8/5246; A61B 8/469; A61B 8/481; A61B 8/5223; A61B 8/488; A61B 8/14; A61B 8/0891; G01B 17/00; G01N 2291/00; G01N 29/00; G01N 2291/02466; G01N 2291/017; G01N 29/2437; G01N 29/2406
    See application file for complete search history.

(56) References Cited

U.S. PATENT DOCUMENTS

| | | | |
|---|---|---|---|
| 6,780,155 B2 | 8/2004 | Li | |
| 7,165,010 B2 | 1/2007 | Mancini et al. | |
| 7,990,379 B2 | 8/2011 | Aharon et al. | |
| 8,094,893 B2* | 1/2012 | Roundhill | A61B 8/06 382/128 |
| 8,187,188 B2 | 5/2012 | Yokota et al. | |
| 8,414,491 B2 | 4/2013 | Kato et al. | |
| 8,529,453 B2 | 9/2013 | Averkiou et al. | |
| 8,708,914 B2 | 4/2014 | Suri | |
| 8,814,798 B2 | 8/2014 | Corbucci et al. | |
| 8,845,542 B2 | 9/2014 | Masuda et al. | |
| 8,852,102 B2 | 10/2014 | Miyachi | |
| 9,357,980 B2 | 6/2016 | Toji et al. | |
| 2003/0114756 A1* | 6/2003 | Li | A61B 8/06 600/437 |
| 2007/0047787 A1 | 3/2007 | Oakley et al. | |
| 2007/0047792 A1 | 3/2007 | Scheuering et al. | |
| 2009/0003675 A1 | 1/2009 | Moreau-Gobard | |
| 2009/0270729 A1* | 10/2009 | Corbucci | A61B 5/0205 600/438 |
| 2011/0150274 A1* | 6/2011 | Patwardhan | G06T 7/0012 382/103 |
| 2011/0208056 A1* | 8/2011 | Datta | A61B 8/06 600/441 |
| 2011/0257527 A1 | 10/2011 | Sun | |
| 2011/0287527 A1 | 11/2011 | Lutz | |
| 2012/0029350 A1* | 2/2012 | Li | A61B 8/06 600/437 |
| 2012/0089025 A1* | 4/2012 | Toji | A61B 8/06 600/443 |
| 2012/0150048 A1 | 6/2012 | Kang et al. | |
| 2013/0016092 A1* | 1/2013 | Collins | A61B 8/0891 345/419 |
| 2013/0046168 A1 | 2/2013 | Sui | |
| 2013/0281855 A1* | 10/2013 | Baba | A61B 8/06 600/441 |
| 2013/0303915 A1* | 11/2013 | Barnard | A61B 8/0891 600/449 |
| 2014/0031690 A1 | 1/2014 | Toji et al. | |
| 2014/0357992 A1 | 12/2014 | Tamada | |
| 2014/0364740 A1 | 12/2014 | Mano | |

FOREIGN PATENT DOCUMENTS

| | | |
|---|---|---|
| JP | 2009160045 A | 7/2009 |
| JP | 2010017523 A | 1/2010 |
| JP | 5016603 B | 9/2012 |
| JP | 2013223625 A | 10/2013 |
| WO | 2012142455 A2 | 10/2012 |
| WO | 2013124946 A1 | 8/2013 |
| WO | 2013129656 A1 | 9/2013 |
| WO | 2014152260 A1 | 9/2014 |

OTHER PUBLICATIONS

2. Tamura Kameda, Evaluation of circulatory dynamics by observation of the inferior vena cava using ultrasonography, Japan Journal of the Emergency Medical Society, vol. 24, No. 11, p. 903-915, 2013.
Murphy, et al., "Evaluation of Wall Motion and Dynamic Geometry of the Inferior Vena Cava Using Intravascular Ultrasound: Implications for Future Device Design", Journal of Endovascular Therapy, vol. 15, Issue 3, Jun. 2008 (Abstract).
Blehar, et al., "Identification of congestive heart failure via respiratory variation of inferior vena cava diameter", American Journal of Emergency Medicine, vol. 27, Issue 1, Jan. 2009, pp. 71-75 (Abstract).
Arthur, et al., "Inferior Vena Cava Diameter (IVCD) Measured with Transesophageal Echocardiography (TEE) can be Used to Derive the Central Venous Pressure (CVP) in Anesthetized Mechanically Ventilated Patients", Echocardiography, vol. 26, Issue 2, Feb. 2009, pp. 140-149 (Abstract).
Schefold, et al., "Inferior Vena Cava Diameter Correlates with Invasive Hemodynamic Measures in Mechanically Ventilated Intensive Care Unit Patients with Sepsis", ScienceDirect, vol. 38, Issue 5, Jun. 2010, pp. 632-637.
Kameda et al Evaluation of the Circulatory Dynamics via Observation of the Inferior Vena Cava Using Ultrasonography Nihon Kyukya Igakukai Zasshi vol. 24, (2013) No. 11, p. 903-915 (with machine translation).
Rudski et al "Guidelines for the Echocardiographic Assessment of the Right Heart in Adults . . . " J. AM SOC. Echocardiogr 2010; 23 p. 685-713.
Goldflam et al "Focus on: Inferior Ven a Cava Ultrasound" ACEP News, Jun. 2011.
"Emergency Ultrasound Guidelines" American College of Emergency Physicians Policy Statement, Oct. 2008.
Feissel et al "The Respiratory Variation in the Inferior Vena Cava Diameter as a Guide to Fluid Therapy" Intensive Care Medicine, (2004) 30: p. 1834-1837.
Perera et al "Cardiac Echocardiographpy" CRIT. Care Clin (2014) p. 47-92.
Zimmermann et al "Accuracy of Stroke Volume Variation Compared With Pleth Variability Index to Predict Fluid Responsiveness in Mechanically Ventilated Patients Undergoing Major Surgery" EUR J. Anaesthesiol, Jun. 27, 2010 p. 555-561.
Lyon et al "Sonographic Measurement of the Inferior Vena Cava as a Marker of Blood Loss" American Journal of Emergency Medicine, (2005) 23, p. 45-50.

(56) References Cited

OTHER PUBLICATIONS

Hofer et al "Assessment of Stroke Volume Variation for Prediction of Fluid Responsiveness Using the Modified Flotrac and Piccoplus System" Critical Care 2008, 12:R82 (doi:10.1186/cc6933).

* cited by examiner

ULTRASOUND SYSTEM AND METHOD OF VESSEL IDENTIFICATION

This application is the U.S. National Phase application under 35 U.S.C. § 371 of International Application No. PCT/EP2016/056984, filed on Mar. 31, 2016, which claims the benefit of Chinese Application No. PCT/CN2015/075831, filed Apr. 3, 2015, and European Application Serial No. 15170630.6, filed Jun. 4, 2015. These applications are hereby incorporated by reference herein.

FIELD OF THE INVENTION

The present invention relates to an ultrasound system and method, particularly to an ultrasound system and method for vessel identification and/or the relevant measurements.

BACKGROUND OF THE INVENTION

Measurements of the diameter of the inferior vena cava (IVC) and its respirophasic variations, called Caval index (CI), using ultrasound have been gaining increasing importance for handling trauma.

Currently, the diameter measurement of a vessel is mostly performed manually or by using semi-automatic segmentation based on seed points manually placed in the vessel region. However, both are user dependent and not preferred in time critical situations, such as EMTs in pre-hospital situations.

US2013/0303915 discloses an automated 3D ultrasound abdominal vessel monitor, which can be used for IVC measurement and monitoring. It claims that the walls of the IVC can be automatically detected so as to determine the size and volume of the IVC. However, the walls of the vessel are not easy to detect because other structures (tissue, bones or other vessels) may impair the detection, and so such a fully automatic approach is not robust or reliable.

SUMMARY OF THE INVENTION

Therefore, it would be advantageous to provide an improved ultrasound system and method for vessel detection and/or identification.

In accordance with an embodiment of a first aspect of the present invention, there is proposed an ultrasound system for identifying a vessel of a subject. The ultrasound system comprises: an ultrasound probe configured to simultaneously acquire a sequence of ultrasound blood flow data frames and a sequence of ultrasound B-mode data frames of a region of interest including the vessel over a predetermined time period; a blood flow region selecting unit configured to detect a blood flow region in each frame of multiple frames in the sequence of ultrasound blood flow data frame, and select a blood flow region among the detected blood flow regions; and a vessel segmenting unit configured to segment the vessel in at least one frame of the sequence of ultrasound B-mode data frames based on the selected blood flow region, the at least one frame comprising the ultrasound B-mode data frame temporally corresponding to the ultrasound blood flow data frame in which the selected blood flow region is detected.

On the one hand, there is no need to manually place any seed point for vessel segmentation, and a fully automatic measurement is achieved, which reduces user dependency and enables a fast measurement. Further, a B-mode data frame is known to be useful and reliable for vessel identification, because it provides various anatomic information, such as the position of the vessel wall. On the other hand, the segmentation of the vessel in a B-mode data frame makes use of information from blood flow data frames, such as Doppler data frames, and thus more robust, reliable segmentation can be achieved. In other words, the selected blood flow region detected in data frames in a certain ultrasound mode, namely ultrasound blood flow data frame, can be served as reliable seed points for further vessel identification on basis of data frames in another ultrasound mode, namely the vessel segmentation in the B-mode data frame. Any existing or future developed, seeds-based segmentation methods can be applied to segment the vessel based on the selected blood flow region. Furthermore, the blood flow region is selected in a sequence of ultrasound blood flow data frames such as a sequence of ultrasound Doppler data frame, namely from multiple data frames acquired at different time points rather than from a single data frame. This is particularly advantageous for identifying a vessel having a blood flow which varies over time, for example, due to the cardiac cycle and/or the respiration cycle, because the blood flow of the vessel might be hardly detectable in a certain data frame but can be reliably detected in at least one data frame of the sequence. For example, the blood flow of the IVC at the expiration phase is more detectable than other phases.

The term "ultrasound blood flow data frame" refers to an ultrasound data frame comprising information on blood flow in the region of interest. The ultrasound blood flow data frame can be an ultrasound Doppler data frame, an ultrasound contrast-enhanced data frame (e.g. data frame acquired in microbubble-assisted imaging), or any other ultrasound data frame acquired by means of any other existing ultrasound modalities or modalities developed in future capable of providing blood flow information. Preferably, an ultrasound Doppler data frame is used alone or in combination with one or more other ultrasound blood flow data frames by the blood flow region selecting unit, because Color Doppler is quite cost efficient.

The person skilled in the art would appreciate that the simultaneously acquired ultrasound B-mode sequence and ultrasound blood flow sequence must not necessarily comprise the same number of data frames. The two sequences may have the same or a different frame rate. In some embodiments, the at least one frame of the sequence of the ultrasound B-mode data frame comprises a frame which is acquired at the same time as the blood flow data frame where the selected blood flow region is located, or a frame which is acquired at a time sufficiently close to the time when the blood flow data frame where the selected blood flow region is located was acquired. During the acquisition of ultrasound data, the ultrasound probe is substantially held steady or stationary so as to acquire ultrasound data from the same region of interest, although the tissue movements may be present due to respiration or the like. The person skilled in the art would also appreciate that the term "B-mode data" is used in a generic sense here and it can be fundamental, harmonic data or any other similar data. Further, the term "segmentation" is also used in a generic sense here and it can refer to the segmentation of all boundaries of the vessel, or it can refer to the segmentation or identification of certain portion(s) of the boundaries.

In some cases, one or more features of the vessel (such as size, blood pressure, blood flow velocity, etc.) periodically change over time, which may, for example, be related to heart cycles or respiration cycles. In those cases, the predetermined time period can preferably cover one or more cycles of the periodical change.

In some embodiments, the vessel can be the vessel of the inferior vena cava or another vessel of interest. The region of interest, the B-mode data frame and the blood flow data frame can be two-dimensional or three-dimensional. In case of being two-dimensional, the region of interest can be either a longitudinal cross section of the vessel, or a transverse cross section of the vessel.

In accordance with an embodiment of the present invention, the blood flow region selecting unit is further configured to determine a size for the detected blood flow regions, and to select the blood flow region based on the determined sizes.

The person skilled in the art would appreciate that the size of the blood flow region can be quantized by various parameters, which can be one or more of area, perimeter, diagonal length, etc. for a two-dimensional region, or can be one or more of volume, cross-sectional area, etc. for a three-dimensional region.

In some embodiments, the size of the selected blood flow region is the largest among the detected blood flow regions. In some other embodiments, any blood flow region having a size larger than a pre-determined threshold can be selected.

In some embodiments, the selection of the blood flow region can be further based on other information such as the orientation of the blood flow, or anatomical information extracted from the B-mode data frames.

In accordance with an embodiment of the present invention, the vessel segmenting unit is further configured to segment the vessel in at least one other frame of the sequence of B-mode data frames by means of tracking the vessel based on the segmented vessel in the at least one frame.

Once the vessel is segmented in one B-mode data frame of the sequence of B-mode data frames, various existing or future developed tracking methods can be applied to track the vessel boundaries in any other B-mode data frame of the sequence. Thus, the vessel can be segmented in any B-mode data frame.

In accordance with an embodiment of the present invention, the ultrasound system further comprises a vessel feature deriving unit configured to derive a feature indicating a transverse size of the segmented vessel in the at least one B-mode data frame. The derived feature can be diameter, transverse cross-section area and other suitable features.

In accordance with an embodiment of the present invention, the ultrasound system further comprises a landmark identifying unit, wherein the landmark identifying unit is configured to identify a landmark in the at least one B-mode data frame; and the vessel feature deriving unit is configured to derive the feature based on the identified landmark.

The transverse size of the vessel may not always be the same, and sometimes the transverse size of a certain portion of the vessel, e.g. a portion proximate a certain landmark, is of particular interest. Thus, by detecting and using certain anatomical landmarks, the corresponding transverse size can be derived.

In some embodiments, the ultrasound system further comprises a display configured to display the derived feature. The derived feature can be presented alone or together with an image of the at least one B-mode data frame. For example, the derived feature can be displayed aside, or overlaid over, the B-mode image.

In accordance with an embodiment of the present invention, the ultrasound system comprises a respiration identifying unit, wherein the respiration identifying unit is configured to identify a respiration cycle of the subject; and the vessel feature deriving unit is configured to derive the feature based on the identified respiration cycle.

For example, the respiration identifying unit is further configured to identify a first data frame of the sequence of ultrasound B-mode data frames corresponding to the end of expiration of the subject and a second data frame of the sequence of ultrasound B-mode data frames corresponding to the end of inspiration of the subject, the vessel segmenting unit is configured to segment the vessel in each of the first and second data frame; and the vessel feature deriving unit is configured to derive the feature based on the segmented vessels in the first and second data frame.

In some embodiments, the respiration identifying unit can be configured to identify the respiration cycle based on a respiration signal received from an additional sensor or extracted from tracking tissue/liver movements.

In some other embodiments, the vessel segmenting unit is configured to segment the vessel in each of a plurality of data frames of the sequence of ultrasound B-mode data frames; and the respiration identifying unit is configured to identify a respiration cycle of the subject based on the segmented vessels in the plurality of data frames. For example, the respiration cycle can be identified based on the features derived from the segmented vessels in the plurality of data frames, such as vessel diameters, or the change of the position of the vessel wall.

In some embodiments, the vessel is the inferior vena cava, the derived features comprise the diameters of the vessel, and the feature deriving unit is further configured to derive the caval index from the derived features.

In accordance with an embodiment of a second aspect of the present invention, there is proposed a first method of identifying a vessel of a subject via ultrasound. The first method comprises the steps of: simultaneously acquiring a sequence of ultrasound blood flow data frames and a sequence of ultrasound B-mode data frames of a region of interest including the vessel over a predetermined time period; detecting a blood flow region in each frame of multiple frames in the sequence of ultrasound blood flow data frame and selecting a blood flow region among the detected blood flow regions; and segmenting the vessel in at least one frame of the sequence of ultrasound B-mode data frames based on the selected blood flow region, the at least one frame comprising the ultrasound B-mode data frame temporally corresponding to the ultrasound blood flow data frame in which the selected blood flow region is detected.

In accordance with an embodiment of a third aspect of the present invention, there is proposed a first apparatus for identifying a vessel of a subject. The first apparatus is connectable to one or more second apparatus for providing a sequence of ultrasound blood flow data and a sequence of ultrasound B-mode data frames of a region of interest including the vessel which are simultaneously acquired over a predetermined time period. The first apparatus comprises: a blood flow region selecting unit configured to detect a blood flow region in each frame of multiple frames in the sequence of ultrasound blood flow data frame, and to select a blood flow region among the detected blood flow regions; and a vessel segmenting unit configured to segment the vessel in at least one frame of the sequence of ultrasound B-mode data frames based on the selected blood flow region, the at least one frame comprising the ultrasound B-mode data frame temporally corresponding to the ultrasound blood flow data frame in which the selected blood flow region is detected.

In accordance with an embodiment of a fourth aspect of the present invention, there is proposed a second method of identifying a vessel of a subject from a sequence of ultrasound blood flow data and a sequence of ultrasound B-mode data frames of a region of interest including the vessel which are simultaneously acquired over a predetermined time period. The second method comprises: detecting a blood flow region in each frame of multiple frames in the sequence of ultrasound blood flow data frame and selecting a blood flow region among the detected blood flow regions; and segmenting the vessel in at least one frame of the sequence of ultrasound B-mode data frames based on the selected blood flow region, the at least one frame comprising the ultrasound B-mode data frame temporally corresponding to the ultrasound blood flow data frame in which the selected blood flow region is detected.

In accordance with an embodiment of a fifth aspect of the present invention, there is proposed a computer product which comprises computer program instructions which, when being executed, perform the aforementioned second method.

Other objects and advantages of the present invention will become more apparent and can be easily understood with reference to the description made in combination with the accompanying drawings.

DESCRIPTION OF THE DRAWINGS

The present invention will be described and explained hereinafter in more detail in combination with embodiments and with reference to the drawings, wherein.

Figure 1:
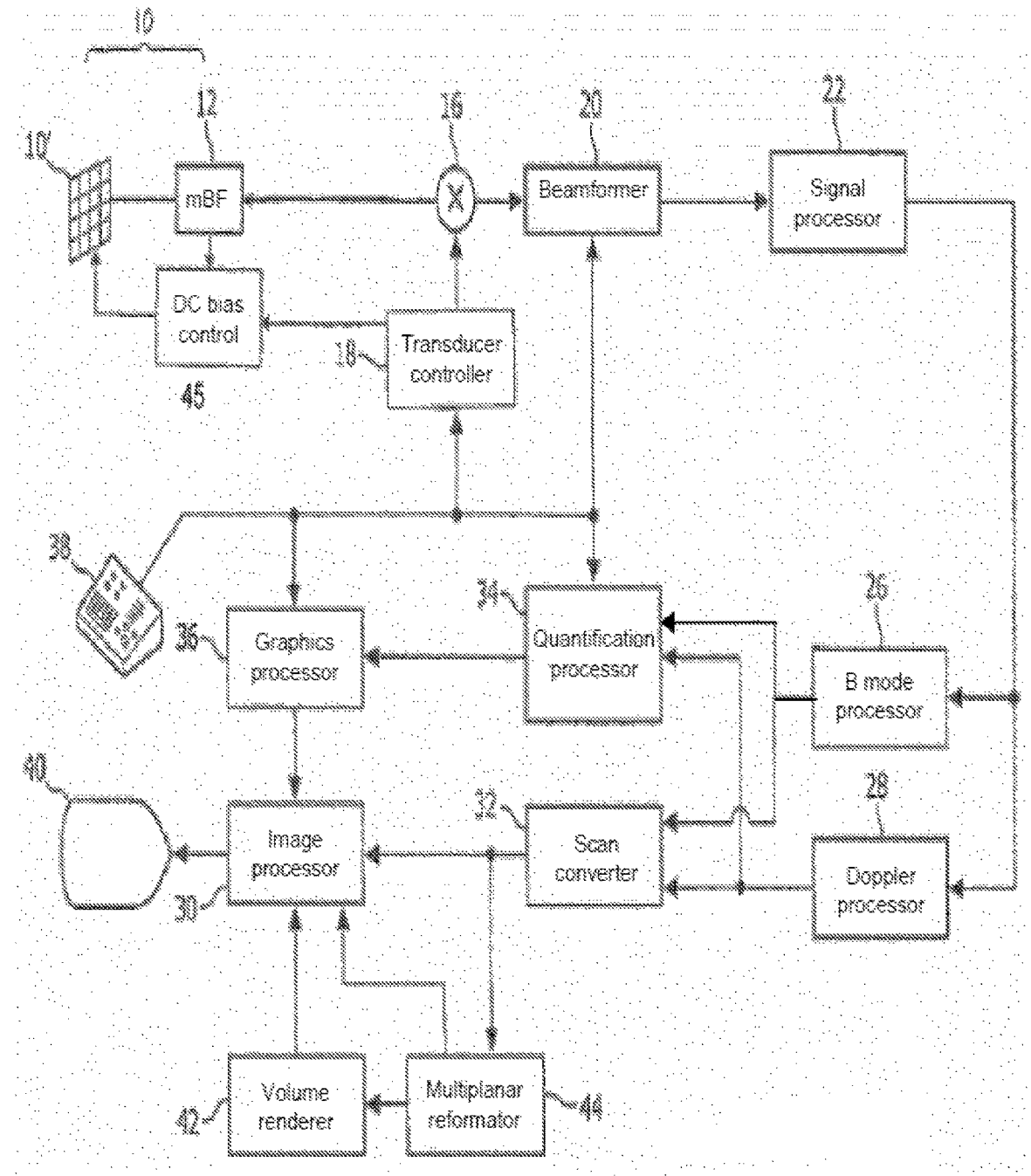
FIG. 1 illustrates in a block diagram form an ultrasound imaging system constructed in accordance with an embodiment of the present invention.

The same reference signs in the figures indicate similar or corresponding features and/or functionalities.

DETAILED DESCRIPTION

The present invention will be described with respect to particular embodiments and with reference to certain drawings but the invention is not limited thereto but only by the claims. For instance, a sequence of ultrasound Doppler data frames is taken as an example of a sequence of ultrasound blood flow data frames, but the skilled person in the art would appreciate that the sequence of ultrasound blood flow data frames can be other sequence of ultrasound data frames comprising blood flow information, such as a sequence of contrast-enhanced data frames. The drawings described are only schematic and are non-limiting. In the drawings, the size of some of the elements may be exaggerated and not drawn to scale for illustrative purposes.

Referring first to FIG. 1, an ultrasonic system with an array transducer probe is shown in block diagram form. In FIG. 1, a CMUT transducer array 10' is provided in an ultrasound probe 10 for transmitting ultrasonic waves and receiving echo information. The transducer array 10' may alternatively comprise piezoelectric transducer elements formed of materials such as PZT or PVDF. The transducer array 10' is a one- or a two-dimensional array of transducer elements capable of scanning in a 2D plane or in three dimensions for 3D imaging. The transducer array is coupled to a microbeamformer 12 in the probe which controls transmission and reception of signals by the CMUT array cells or piezoelectric elements. Microbeamformers are capable of at least partial beamforming of the signals received by groups or "patches" of transducer elements as described in U.S. Pat. No. 5,997,479 (Savord et al.), U.S. Pat. No. 6,013,032 (Savord), and U.S. Pat. No. 6,623,432 (Powers et al.) The microbeamformer is coupled by the probe cable to a transmit/receive (T/R) switch 16 which switches between transmission and reception and protects the main beamformer 20 from high energy transmit signals when a microbeamformer is not used and the transducer array is operated directly by the main system beamformer. The transmission of ultrasonic beams from the transducer array 10 under control of the microbeamformer 12 is directed by a transducer controller 18 coupled to the microbeamformer by the T/R switch and the main system beamformer 20, which receives input from the user's operation of the user interface or control panel 38. One of the functions controlled by the transducer controller is the direction in which beams are steered and focused. Beams may be steered straight ahead from (orthogonal to) the transducer array, or at different angles for a wider field of view. The transducer controller 18 can be coupled to control a DC bias control 45 for the CMUT array. The DC bias control 45 sets (a) DC bias voltage(s) that is/are applied to the CMUT cells.

The partially beamformed signals produced by the microbeamformer 12 on receive are coupled to a main beamformer 20 where partially beamformed signals from individual patches of transducer elements are combined into a fully beamformed signal. For example, the main beamformer 20 may have 128 channels, each of which receives a partially beamformed signal from a patch of dozens or hundreds of CMUT transducer cells or piezoelectric elements. In this way the signals received by thousands of transducer elements of a transducer array can contribute efficiently to a single beamformed signal.

The beamformed signals are coupled to a signal processor 22. The signal processor 22 can process the received echo signals in various ways, such as bandpass filtering, decimation, I and Q component separation, and harmonic signal separation which acts to separate linear and nonlinear signals so as to enable the identification of nonlinear (higher harmonics of the fundamental frequency) echo signals returned from tissue and microbubbles. The signal processor may also perform additional signal enhancement such as speckle reduction, signal compounding, and noise elimination. The bandpass filter in the signal processor can be a tracking filter, with its passband sliding from a higher frequency band to a lower frequency band as echo signals are received from increasing depths, thereby rejecting the noise at higher frequencies from greater depths where these frequencies are devoid of anatomical information.

The processed signals are coupled to a B mode processor 26 and a Doppler processor 28. The B mode processor 26 employs detection of an amplitude of the received ultrasound signal for the imaging of structures in the body such as the tissue of organs and vessels in the body. B mode images of structures of the body may be formed in either the harmonic image mode or the fundamental image mode or a combination of both as described in U.S. Pat. No. 6,283,919 (Roundhill et al.) and U.S. Pat. No. 6,458,083 (Jago et al.) The Doppler processor 28 processes temporally distinct signals from tissue movement and blood flow for the detection of the motion of substances such as the flow of blood cells in the image field. The Doppler processor typically includes a wall filter with parameters which may be set to pass and/or reject echoes returned from selected types of materials in the body. For instance, the wall filter can be set to have a passband characteristic which passes signals of relatively low amplitude from higher velocity materials while rejecting relatively strong signals from lower or zero velocity material. This passband characteristic will pass signals from flowing blood while rejecting signals from nearby stationary or slowing moving objects such as the wall of the heart. An inverse characteristic would pass signals from moving tissue of the heart while rejecting blood flow signals for what is referred to as tissue Doppler imaging, detecting and depicting the motion of tissue. The Doppler processor receives and processes a sequence of temporally discrete echo signals from different points in an image field, the sequence of echoes from a particular point referred to as an ensemble. An ensemble of echoes received in rapid succession over a relatively short interval can be used to estimate the Doppler shift frequency of flowing blood, with the correspondence of the Doppler frequency to velocity indicating the blood flow velocity. An ensemble of echoes received over a longer period of time is used to estimate the velocity of slower flowing blood or slowly moving tissue.

The structural and motion signals produced by the B mode and Doppler processors are coupled to a scan converter 32 and a multiplanar reformatter 44. Volume renderer 42 is coupled to an image processor 30 for further enhancement, buffering and temporary storage for display on an image display 40.

Alternative or additional to being used for imaging, the blood flow values produced by the Doppler processor 28 and tissue structure information produced by the B mode processor 26 are coupled to a quantification processor 34. Optionally, the quantification processor may receive input from the user control panel 38, such as the point in the anatomy of an image where a measurement is to be made. Output data from the quantification processor can be coupled to a graphics processor 36 for the reproduction of measurement graphics and values with the image on the display 40. The graphics processor 36 can also generate graphic overlays for display with the ultrasound images. These graphic overlays can contain standard identifying information such as patient name, date and time of the image, imaging parameters, and the like.

The skilled person in the art would appreciate that the scan converter 32, the multiplaner reformater 44, volume renderer 42, image processor can be omitted in some embodiments if no ultrasound image is to be displayed.

In accordance with an embodiment of the present invention, the ultrasound probe 10 is configured to simultaneously acquire a sequence of ultrasound Doppler data frames and a sequence of ultrasound B-mode data frames of a region of interest including the vessel, and the quantification processor 32 comprises a blood flow region selecting unit configured to determine the size of one or more blood flow regions in the sequence of ultrasound Doppler data frames, and to select a blood flow region based on the determined size; and a vessel segmenting unit configured to segment the vessel based on the selected blood flow region. In other words, the quantification processor 32 acts as the apparatus 200 of FIG. 2.

Figure 2:
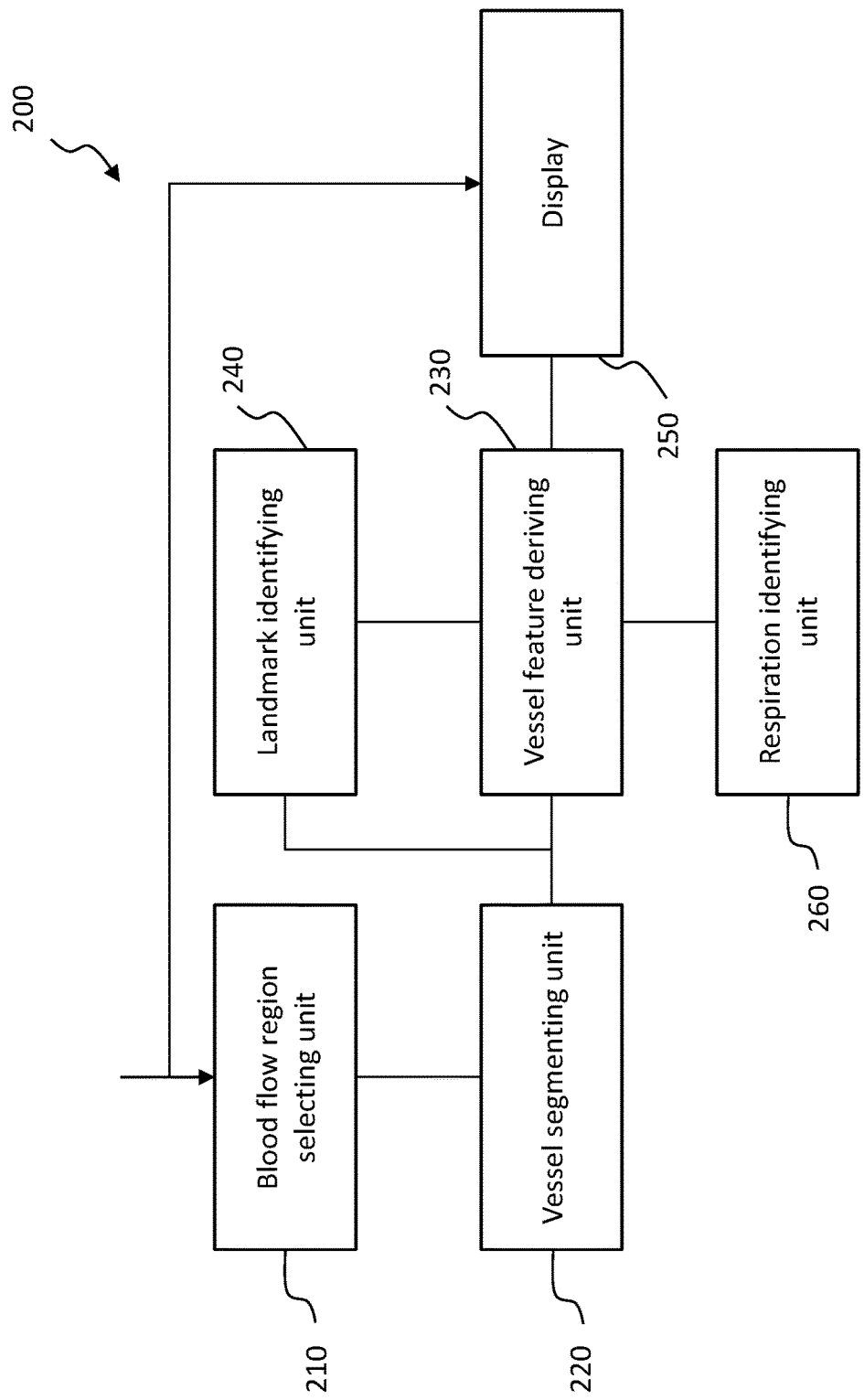
FIG. 2 illustrates in a block diagram form a first apparatus for identifying a vessel of a subject in accordance with an embodiment of the present invention.

FIG. 2 illustrates in a block diagram form a first apparatus 200 for identifying a vessel of a subject in accordance with an embodiment of the present invention. The first apparatus 200 can be part of any ultrasound device. Alternatively, the first apparatus 200 can be a separate device which is connectable to one or more second apparatus for providing simultaneously acquired sequence of ultrasound Doppler data and sequence of ultrasound B-mode data frames of a region of interest including the vessel. The second apparatus can be an ultrasound system, an ultrasound device, an ultrasound probe, a clinical information system, or any other kind of apparatus capable of providing ultrasound data, for example in DICOM format or in any other suitable format like RF signal format.

Referring to FIG. 2, the first apparatus 200 comprise a blood flow region selecting unit 210, a vessel segmenting unit 220, a vessel feature deriving unit 230, a landmark identifying unit 240, a display 250, and a respiration identifying unit 260.

Figure 3:
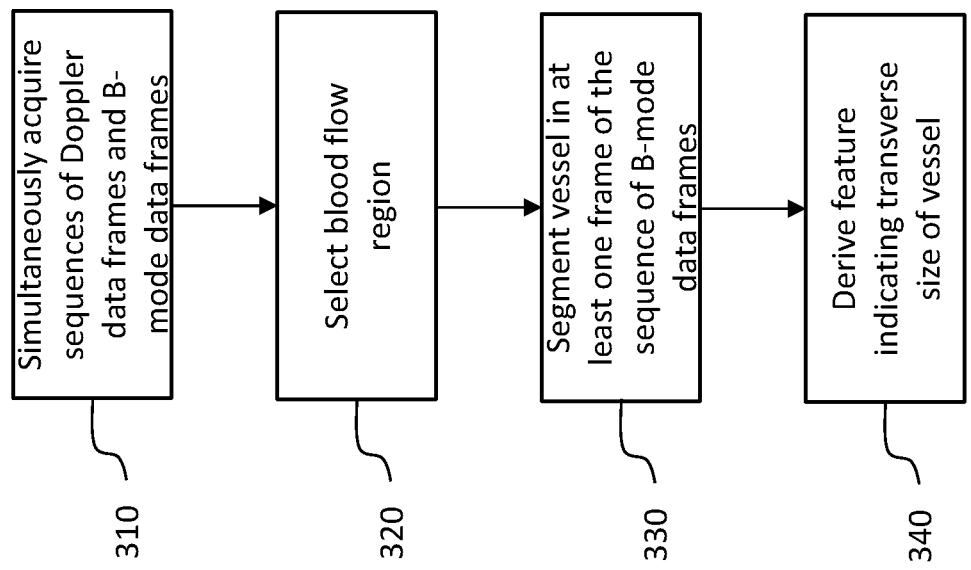
FIG. 3 illustrates in a block diagram a method of identifying a vessel of a subject in accordance with an embodiment of the present invention.

FIG. 3 illustrates in a block diagram a method of identifying a vessel of a subject in accordance with an embodiment of the present invention.

In step 310, the ultrasound probe 10 simultaneously acquires a sequence of ultrasound Doppler data frames and a sequence of ultrasound B-mode data frames of a region of interest including the vessel over a predetermined time period.

In step 320, the blood flow region selecting unit 210 selects a blood flow region in the sequence of Doppler data frames. In other words, the blood flow region is selected among multiple data frames acquired at different time rather than from a single data frame. In particular, the blood flow region selecting unit 210 is configured to detect any blood flow region in each of multiple data frames in the sequence of ultrasound blood flow frames. The multiple data frames can be all data frames or a subset of data frames in the sequence of ultrasound blood flow frames.

In some embodiments, the blood flow region selecting unit 210 is further configured to determine a size for the detected blood flow regions in the sequence of ultrasound Doppler data frames, and to select the blood flow region based on the determined size. For example, the blood flow region having the largest area or perimeter among the detected blood flow regions is selected.

Figure 4A:
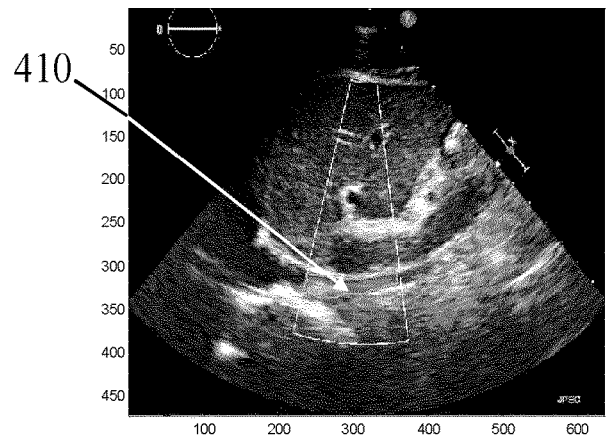
FIG. 4(a) to FIG. 4(d) each illustrate an exemplary B-mode image overlaid with the blood flow regions detected in the blood flow data frame in different respiration phases, wherein FIG. 4(a) and FIG. 4(d) respectively correspond to inspiration and expiration.
Figure 4B:
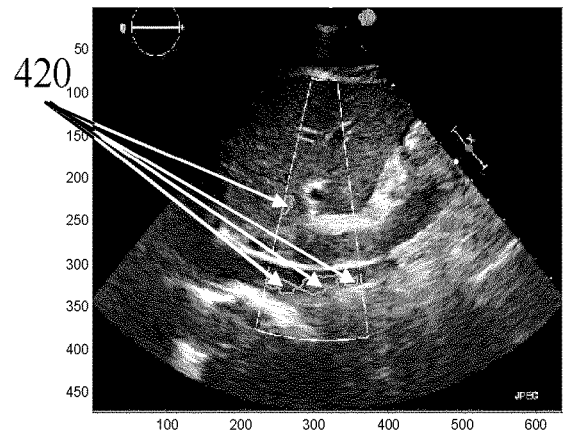
Figure 4C:
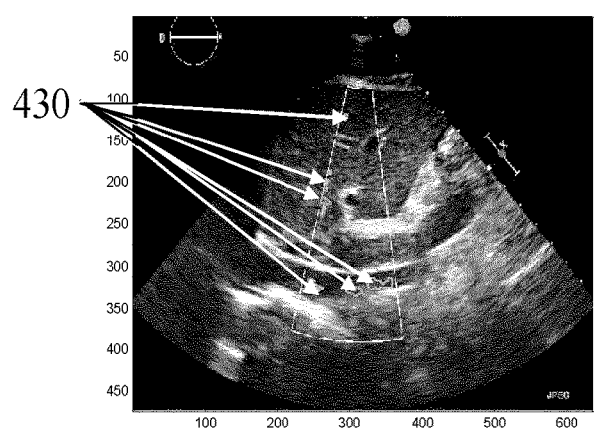
Figure 4D:
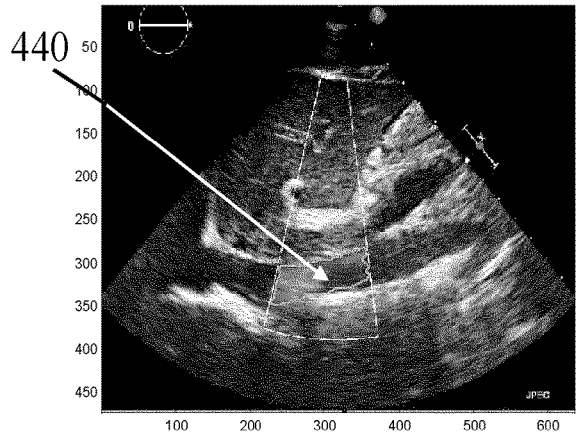

FIG. 4(a) to FIG. 4(d) each illustrate an exemplary B-mode image overlaid with the blood flow regions detected in the temporally corresponding Doppler data frame acquired at a different time corresponding to different respiration phases, wherein FIG. 4(a) and FIG. 4(d) respectively correspond to inspiration and expiration. In FIG. 4(a) to FIG. 4(d), the detected blood flow regions are depicted as the enclosed regions 410, 420, 430, 440, respectively. In this example, the region of interest comprises a longitudinal (head-feet direction) cross section of the IVC of a subject. More than one blood flow regions can be detected in a single ultrasound Doppler data frame. The more than one blood flow regions can belong to the same vessel or different vessels. As described in the above, in some embodiments, the blood flow region having the largest area or perimeter among the detected blood flow regions is selected. In this example, the blood flow region 440 in the Doppler data frame illustrated in FIG. 4(*d*) is selected.

In some other embodiments, in addition to the size of the detected blood flow region, the blood flow regions can be selected by further taking one or more other intrinsic characteristics of the vessel to be identified into account, which is useful in differentiating the blood flow region corresponding to the vessel of interest from other blood flow regions corresponding to other vessels or tissues. Taking the IVC for an example, one or more of the following can be used: color Doppler pattern, pulsating pattern/pulse wave velocity (PWV) of IVC walls, echogenicity/thickness of the IVC wall, flow pattern in the IVC (the IVC's distal wall being in close proximity to the aorta sometimes exhibits a beating pattern similar to that of the aorta's walls), or advance image processing technique, e.g., searching for the horn-like region (noting that the IVC is of a horn-like shape when imaged longitudinally) or for the half-moon-like dark region in the image (noting that the right atrium presents itself as a dark half-moon-like area in the longitudinal IVC image).

In step 330, the vessel segmenting unit segments the vessel in at least one frame of the sequence of ultrasound B-mode data frames based on the selected blood flow region. In particular, the vessel segment is performed in an ultrasound B-mode data frame temporally corresponding to the ultrasound blood flow data frame in which the selected blood flow region is detected. In some embodiments, the vessel segments can be further performed in the ultrasound B-mode data frame adjacent to the temporally corresponding B-mode data frame.

Here, the term "temporally corresponding" means that the ultrasound B-mode data frame is acquired at the same time as the ultrasound blood flow data frame, or is acquired at a time closest to the acquisition time of the ultrasound blood flow data frame among all ultrasound B-mode data frames.

Since the sequence of ultrasound B-mode data frames and the sequence of ultrasound blood flow data frames are acquired simultaneously, the B-mode data frame and the blood flow data frame acquired at the same or close time are also substantially registered to each other. Thus, once the position of the selected blood flow region is known in the ultrasound blood flow data frame, its corresponding position in the ultrasound B-mode data frame is also known and can be used as seeds for segmentation in the ultrasound B-mode data frame. That is, the vessel segmentation in the ultrasound B-mode data frame can be performed by using the position of the blood flow region detected in ultrasound blood flow data frame as seeds.

In some embodiments, one or more pixels, such as the centroid, in the selected blood flow region, are used as seeds for segmentation.

In some embodiments, the vessel segmenting unit is configured to select, among the sequence of the ultrasound B-mode data frames, the ultrasound B-mode data frame which temporally corresponds to the ultrasound blood flow data frame in which the selected blood flow region is detected, to identify, in the selected ultrasound B-mode data frame, a region which spatially corresponding to the selected blood flow region in the ultrasound blood flow data frame, and to segment the vessel in the selected ultrasound B-mode data frame by using the identified region as seeds. For example, the identified region comprises pixels spatially corresponding to one or more pixels, such as the centroid, in the selected blood flow region.

Various existing or future developed, seeds-based segmentation methods can be applied to segment the vessel based on the selected blood flow region. In the results illustrated in FIG. 5, a similarity-based region growing method is to segment the IVC. The searching can be based on the similarity in grayscale, texture or color Doppler. Once the edges are detected, the searching in the up and down directions stops and continues in lateral directions along the IVC boundaries. The searching proceeds until the distance between the upper and lower edges gets larger or smaller than a threshold, e.g., in case the searching goes into the atrium.

Once the vessel is segmented in one B-mode data frame of the sequence of B-mode data frames, various existing or future developed tracking method can be applied to track the vessel boundaries in any other B-mode data frame of the sequence. Thus, in some embodiments, the vessel segmenting unit is further configured to segment the vessel in at least one other frame of the sequence of B-mode data frames by means of tracking the vessel based on the segmented vessel in the at least one frame.

In step 340, the vessel feature deriving unit 230 derives a feature indicating a transverse size of the segmented vessel in the at least one B-mode data frame. For example, the derived feature can be a diameter, transverse cross-section area and other suitable feature. The derived feature can be presented, via the display 250, alone or together with an image of the at least one B-mode data frame. In an example, the derived feature can be displayed aside, or overlaid over, the B-mode image. In another example, the derived feature can be displayed without displaying any image. In another example, the derived feature is not displayed, but an indication such as an alarm can be presented via any suitable user interface when the derived feature fulfills a pre-determined criterion, which could be particularly advantageous for monitoring purposes.

In some embodiments, the movements of both the upper and lower walls of the vessel are tracked, e.g., using a normalized cross correlation (cc) algorithm or other suitable algorithms. The tracking can be realized by applying a cc algorithm to either adjacent frames continuously, or every frame and the frame in which the wall of the vessel is segmented based on the selected blood flow regions. The cc algorithm can be applied to the whole region of interest, or alternatively to a region which contains the vessel boundary. The latter is more computationally efficient than the former. With the movement of both walls of the vessel, the vessel diameter is updated in real time based on the value that was measured in the earlier step.

Figure 5:
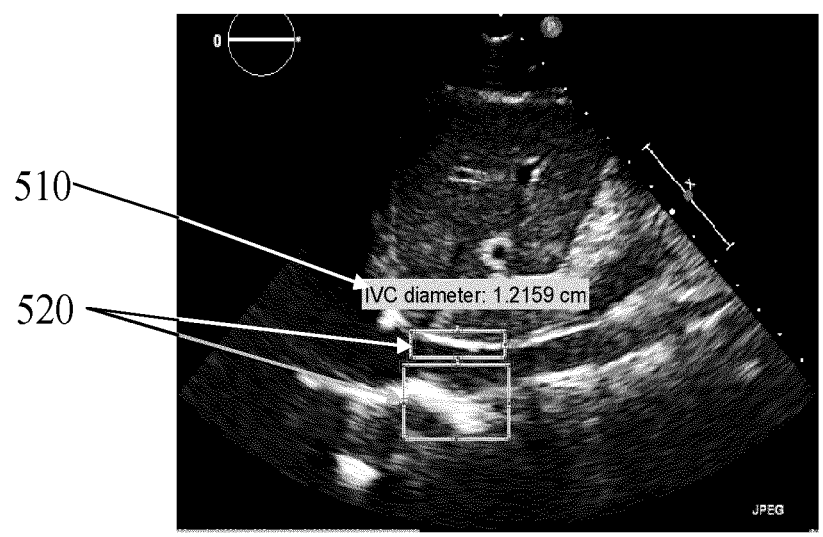
FIG. 5 illustrates an exemplary B-mode image overlaid with the tracked vessel boundaries and the diameter of the vessel.

FIG. 5 illustrates an exemplary B-mode image overlaid with the tracked vessel boundaries and the diameter of the vessel. In FIG. 5, the two rectangular boxes 520 illustrate the tracked upper and lower wall of the IVC, and the derived IVC diameter in this B-mode data frame is also presented (see 510).

In some embodiments, the steps 320 to 340 can be performed during a continuous acquisition of the sequence of B-mode data frames, and once the vessel is segmented in at least one B-mode data frame, the tracked vessel walls and/or the derived vessel features can be presented in real time during the acquisition of the ultrasound sequence.

In case that the vessel is the inferior vena cava, the feature deriving unit 230 can be further configured to derive the caval index from the derived vessel diameters. In an example, the caval index can be calculated as (the maximum of the IVC diameter−the minimum of the IVC diameter)/the maximum of the IVC diameter*100, and in another example, if provided with the respiration information, the caval index can be calculated as (IVC expiratory diameter−IVC inspiratory diameter)/IVC expiratory diameter*100.

Additionally or alternatively, the feature deriving unit 230 can be configured to detect the collapse of the vessel such as IVC. The collapse of the vessel can be detected in various manners in accordance with various embodiments.

In an embodiment, the vessel is detected to be collapsed if the movement of the boundaries of the vessel in a pair of adjacent frames is detected to be greater than a first predetermined threshold, such as two times of the vessel diameter, which actually indicates the tracking of the movements of the boundaries of the vessel become failed. Taking an IVC as an exemplary vessel, Table 1 illustrates the tracked movement of the upper wall of the longitudinal cross section of the vessel in an experiment. In case that the IVC is not collapsed, the boundary of the IVC can be tracked to continuously move with respiration. Once the IVC is fully collapsed, the boundaries of the IVC become vanish or indistinguishable, and thus the tracking results become random and chaotic, resulting in that the tracked movement of the vessel boundaries is much greater than the normal range.

TABLE 1

Movement of the upper wall in vertical direction before and after collapse in a series of continuous frames (Pig 05 at Hypo-10%)

| | Before collapse | | | | After collapse | | | | |
|---|---|---|---|---|---|---|---|---|---|
| | Frame No. | | | | | | | | |
| | 80 | 81 | 82 | 83 | 84 | 85 | 86 | 87 | 88 |
| Movement of upper wall [cm] | 0 | 0.02 | −0.01 | 0.01 | 0.5 | 2.32 | 3.62 | 4.81 | 3.94 |

In another embodiment, the vessel is detected to be collapsed if the derived size of the vessel, such as the diameter of the vessel, is detected to be decreasing and approaching zero in the past several frames. In an example, the vessel is detected to be collapsed if the derived size of the vessel is smaller than a second predetermined threshold. In another example, the vessel is detected to be collapsed if the tracked movement of the vessel boundaries between the current frame and the previous frame become larger than the first predetermined threshold and the size of the vessel in past several frames is decreasing.

Prior to the feature derivation, the landmark identifying unit 240 can identify a landmark in the at least one B-mode data frame, and then the vessel feature deriving unit 230 is configured to derive the feature based on the identified landmark. The landmark can be used to determine a suitable portion of the vessel for tracking and deriving the feature. In case that the vessel is the IVC, the landmark can be the hepatic vein, right atrium and/or diaphragm. For example, the IVC walls located at 2 cm from the position where the IVC attaches to the right atrium is a suitable portion of the vessel for deriving the feature.

Figure 6:
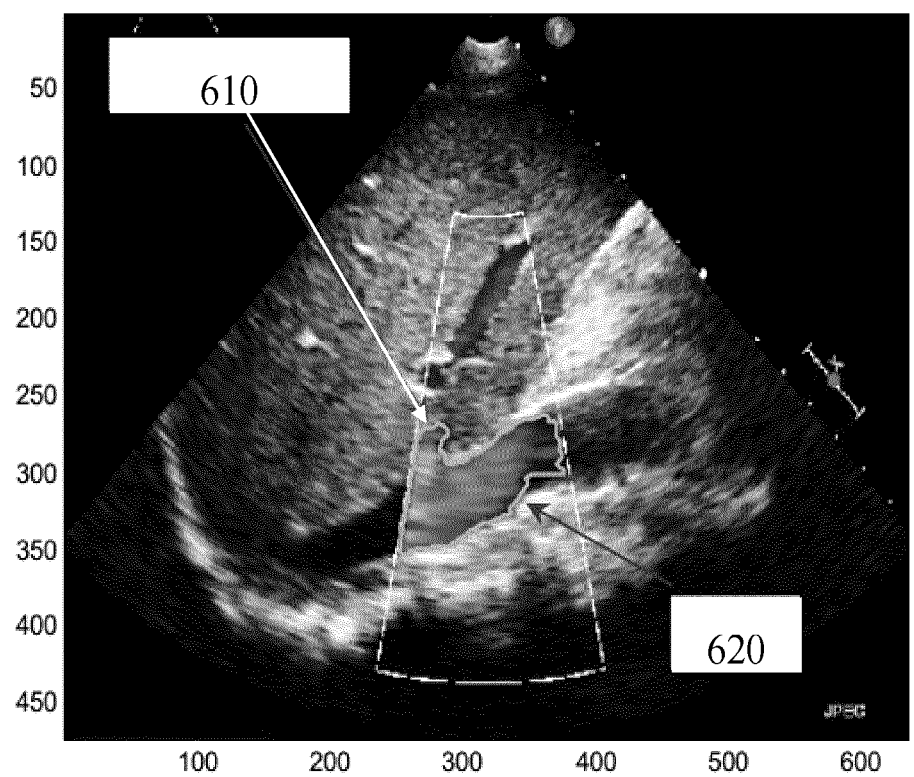
FIG. 6 illustrates an exemplary B-mode image overlaid with the identified hepatic vein as landmark.

FIG. 6 illustrates an exemplary B-mode image overlaid with the identified hepatic vein 610 as landmark. In this example, a Doppler data frame is used to identify the hepatic veins. Sometimes, the hepatic vein may be impaired by other veins or the aorta. Alternatively or additionally, the identification of the hepatic vein can be achieved by using intrinsic characteristics of the hepatic vein, including pulsation pattern, fluid pattern, absence of wall echogenicity, etc. In addition, the hepatic vein in conjunction with the IVC can be further identified by identifying the IVC first and then searching along the IVC. In FIG. 6, the IVC 620 and the hepatic vein 610 as well as their conjunction are clearly illustrated.

Figure 7A:
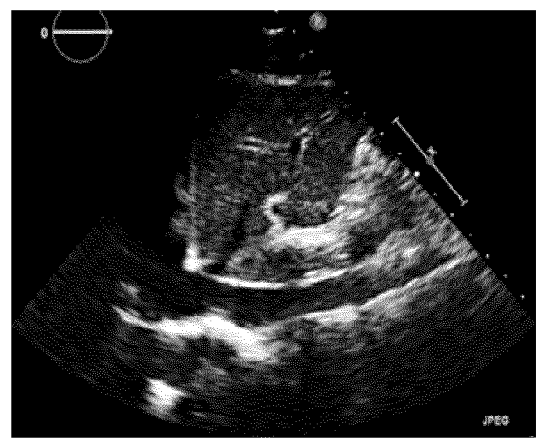
FIG. 7(a) to FIG. 7(b) illustrate the detection of the conjunction of right atrium and IVC as landmark.
Figure 7B:
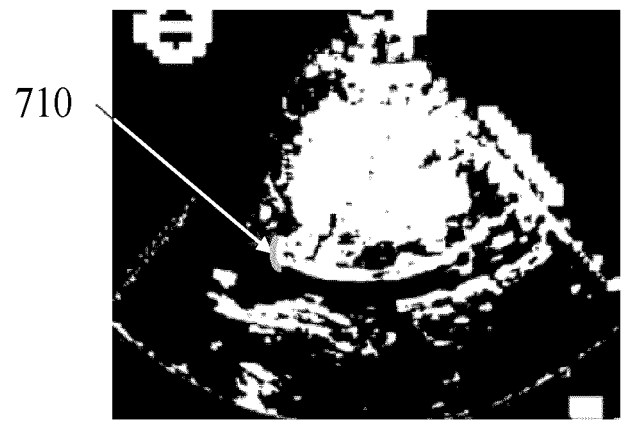

FIG. 7(a) and FIG. 7(b) illustrate the detection of the conjunction of right atrium and IVC as landmark. In this example, the boundary of the right atrium is identified using a cross correlation algorithm. The heuristic is that echoes from blood in the right atrium are non-stationary in the sense that the scatters in the tissue are in constant motion. Hence, if a cross correlation is performed between two frames of data, regions of blood show a low correlation, or a speckle-like variation of correlation. Such a pattern is absent in normal tissue. FIG. 7(a) is a B-mode image of a B-mode data frame; FIG. 7(b) is a binary image derived by applying a threshold to the cc map of two B-mode data frames. The identified conjunction 710 of the right atrium/diaphragm and the IVC is also illustrated in FIG. 7(b). The identification of the conjunction 710 of the right atrium/diaphragm and the IVC can be achieved in various ways. For example, it can be achieved by first searching the upper wall edge of the IVC in both lateral directions. When a significant change in the direction or angles of the edge occurs at a certain position, such a position is detected as the joint point of the right atrium and the IVC.

In accordance with an embodiment of the present invention, the respiration identifying unit 260 is configured to identify a respiration cycle of the subject, and the vessel feature deriving unit is configured to derive the feature based on the identified respiration cycle. For example, the inspiratory IVC diameter, the expiratory diameter, and/or the caval index can be derived using the identified respiration cycle.

In some embodiments, the respiration identifying unit 260 can be configured to identify the respiration cycle based on a respiration signal received from an additional sensor or extracted from tracking tissue/liver movements.

In some other embodiments, the vessel segmenting unit is configured to segment the vessels in each of a plurality of data frames of the sequence of ultrasound B-mode data frames; and the respiration identifying unit is configured to identify a respiration cycle of the subject based on the segmented vessels in the plurality of data frames. For example, the respiration cycle can be identified based on the features derived from the segmented vessels, such as vessel diameters, or the change of the position of the vessel wall.

Figure 8A:
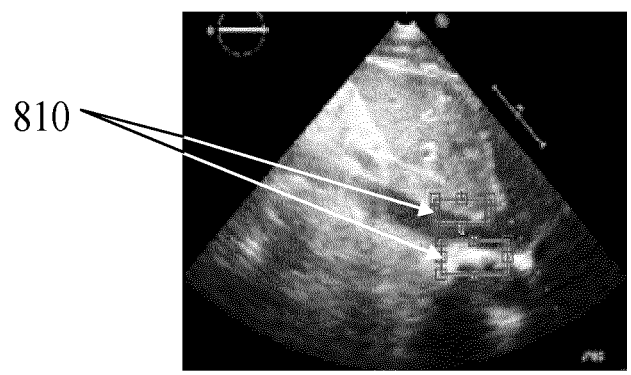
FIG. 8(a) illustrates an exemplary B-mode image overlaid with the tracked vessel boundaries.
Figure 8B:
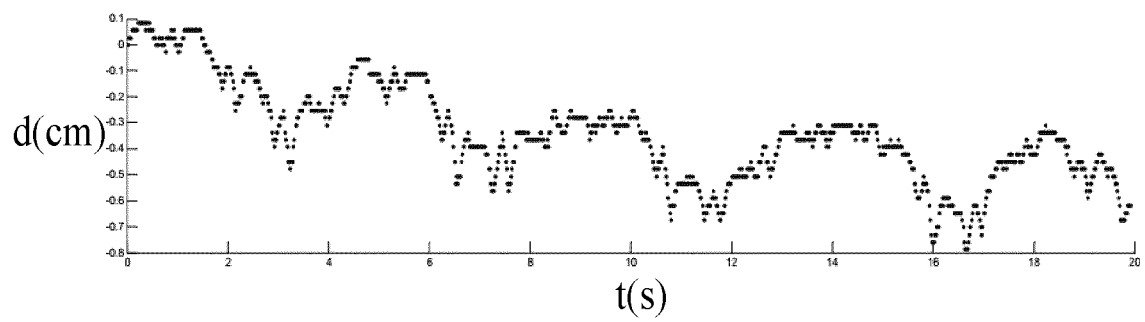
FIG. 8(b) illustrates the change of the vessel's diameter, in unit of cm, over time in unit of second.

FIG. 8(a) illustrates an exemplary B-mode image overlaid with the tracked IVC boundaries, FIG. 8(b) illustrates the change of the IVC's diameter, in unit of cm, over time in unit of second.

Figure 9A:
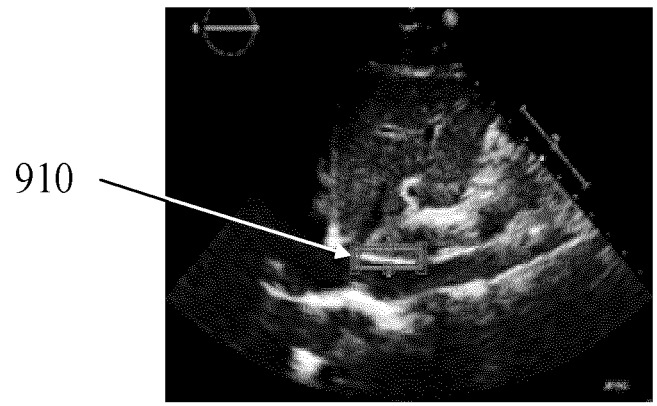
FIG. 9(a) illustrates an exemplary B-mode image overlaid with the tracked vessel's upper boundary.
Figure 9B:
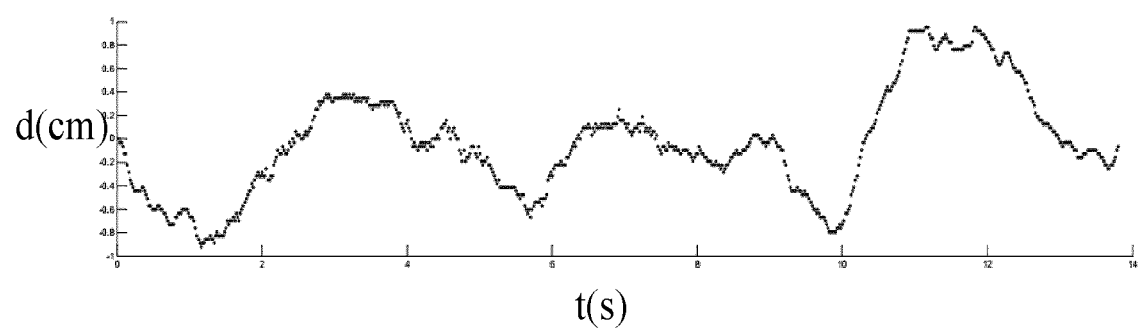
FIG. 9(b) illustrates the change of the position of the vessel's upper boundary, in unit of cm, over time in unit of second.
Figure 10A:
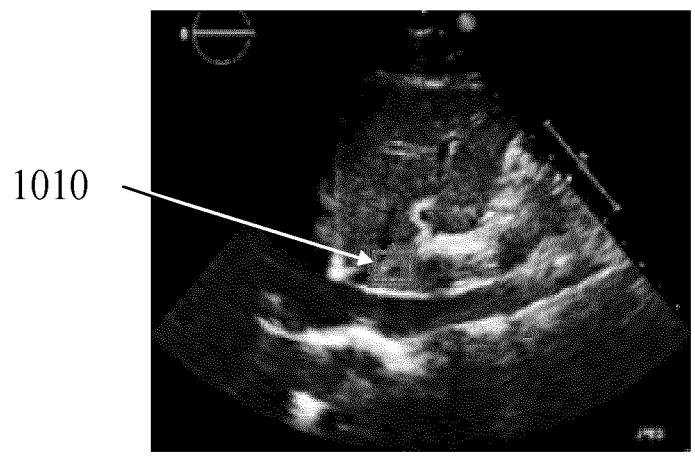
FIG. 10(a) illustrates an exemplary B-mode image overlaid with the tracked liver tissue.
Figure 10B:
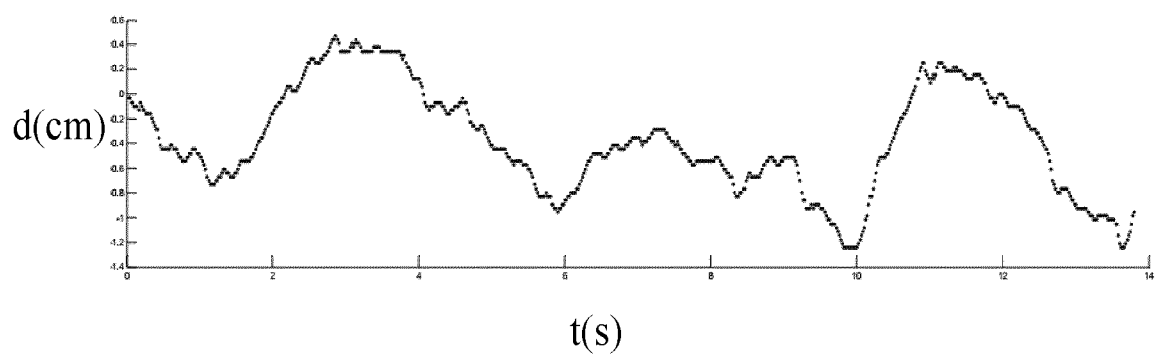
FIG. 10(b) illustrates the change of the position of the liver tissue, in unit of cm, over time in unit of second.

FIG. 9(a) illustrates an exemplary B-mode image overlaid with the tracked IVC's upper boundary, FIG. 9(b) illustrates the change of the position of the IVC's upper boundary, in unit of cm, over time in unit of second; and FIG. 10(a) illustrates an exemplary B-mode image overlaid with the tracked liver tissue, FIG. 10(b) illustrates the change of the position of the liver tissue, in unit of cm, over time in unit of second.

From FIG. 8(b), FIG. 9(b), FIG. 9(c), it can be shown that a respiration cycle can be derived from the change of the IVC diameter, the movement of the IVC boundary or the movement of the liver tissue.

The technique processes described herein may be implemented by various means. For example, these techniques may be implemented in hardware, software, or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein, or a combination thereof. With software, implementation can be through modules (e.g., procedures, functions, and so on) that perform the functions described herein. The software codes may be stored in a memory unit and executed by the processors.

Moreover, aspects of the claimed subject matter may be implemented as a method, apparatus, system, or article of manufacture using standard programming and/or engineering techniques to produce software, firmware, hardware, or any combination thereof to control a computer or computing components to implement various aspects of the claimed subject matter. The term "article of manufacture" as used herein is intended to encompass a computer program accessible from any computer-readable device, carrier, or media. For example, computer readable media can include but are not limited to magnetic storage devices (e.g., hard disk, floppy disk, magnetic strips . . . ), optical disks (e.g., compact disk (CD), digital versatile disk (DVD) . . . ), smart cards, and flash memory devices (e.g., card, stick, key drive . . . ). Of course, those skilled in the art will recognize that many modifications may be made to this configuration without departing from the scope or spirit of what is described herein.

As used in this application, the term "unit" such as "blood flow region selecting unit", "vessel segmenting unit", "vessel feature deriving unit", "landmark identifying unit", "respiration identifying unit" are intended to refer to a processor or a computer-related entity, either hardware, a combination of hardware and software, software, or software in execution. For example, a component may be, but is not limited to, a process running on a processor, a processor, an object, an executable, a thread of execution, a program, and/or a computer. By way of illustration, both an application running on a server and the server can be a component. One or more components may reside within a process and/or thread of execution and a component may be localized on one computer and/or distributed among two or more computers.

What has been described above includes examples of one or more embodiments. It is, of course, not possible to describe every conceivable combination of components or methodologies for the purpose of describing the aforementioned embodiments, but one of ordinary skill in the art may recognize that many further combinations and permutations of various embodiments are possible. Accordingly, the described embodiments are intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

The invention claimed is:

1. An ultrasound system for identifying a vessel of a subject, comprising:
    an ultrasound probe; and
    a processor communicatively coupled to and configured to control the ultrasound probe to simultaneously acquire a sequence of ultrasound blood flow data frames and a sequence of ultrasound B-mode data frames of a region of interest including the vessel over a predetermined time period, wherein the region of interest comprises a longitudinal cross section of a length of the vessel and a landmark that is different than the vessel, and wherein the processor comprises:
        a blood flow region selecting unit configured to detect a blood flow region indicating a blood flow along the length of the vessel in each frame of multiple frames in the sequence of ultrasound blood flow data frames, and to select a blood flow region among the detected blood flow regions based on a frame of the multiple frames in which the blood flow region is larger than a threshold;
        a vessel segmenting unit configured to segment the vessel in at least one frame of the sequence of ultrasound B-mode data frames based on the selected blood flow region, the at least one frame comprising the ultrasound B-mode data frame temporally corresponding to the ultrasound blood flow data frame in which the selected blood flow region is detected, wherein the vessel segmenting unit is configured to identify an upper wall and a lower wall along the length of the vessel, and wherein the segmenting is based on seed points automatically derived from the selected blood flow region;
        a landmark identifying unit configured to automatically identify the landmark in the at least one frame; and
        a vessel feature deriving unit configured to derive, based on the identified landmark, a feature indicating a transverse size of the segmented vessel corresponding to a distance between the upper wall and the lower wall in each of the at least one frame,
    wherein the landmark identifying unit is configured to identify a longitudinal portion along the length of the vessel at which the feature is derived, and
    wherein the vessel feature deriving unit is configured to detect a collapse of the vessel at a location of the vessel based on at least one of:
        the distance between the upper wall and lower wall falling below a predetermined threshold at that location; or
        a change in the distance between the upper wall and lower wall exceeding a predetermined threshold at that location.

2. The ultrasound system of claim 1, wherein the blood flow region selecting unit is further configured to determine a size for each of the detected blood flow regions, and to select the blood flow region based on the determined sizes.

3. The ultrasound system of claim 2, wherein the size of the selected blood flow region is the largest size among the detected blood flow regions.

4. The ultrasound system of claim 1, wherein the vessel segmenting unit is further configured to segment the vessel in at least one other frame of the sequence of B-mode data frames by means of tracking the vessel based on the segmented vessel in the at least one frame.

5. The ultrasound system of claim 1, wherein the processor further comprises a respiration identifying unit, wherein the respiration identifying unit is configured to identify a respiration cycle of the subject; and
the vessel feature deriving unit is configured to derive the feature based on the identified respiration cycle.

6. The ultrasound system of claim 5, wherein
the vessel segmenting unit is configured to segment the vessel in each of a plurality of data frames of the sequence of ultrasound B-mode data frames; and
the respiration identifying unit is configured to identify the respiration cycle of the subject based on the segmented vessels in the plurality of data frames.

7. The ultrasound system of claim 1, the ultrasound blood flow data frame is an ultrasound Doppler data frame.

8. The ultrasound system of claim 1, wherein the vessel is an inferior vena cava.

9. The ultrasound system of claim 1, wherein the region of interest is two-dimensional.

10. The system of claim 1, wherein the vessel feature deriving unit is configured to derive the feature at a first location in the vessel based on a second location of the identified landmark.

11. The system of claim 10, wherein the identified landmark is a hepatic vein.

12. The system of claim 1, wherein the at least one frame comprising the ultrasound B-mode data frame is acquired at a same time as the ultrasound blood flow data frame in which the selected blood flow region is detected.

13. A method of identifying a vessel of a subject, comprising steps of:
controlling, by a processor, an ultrasound probe to simultaneously acquire a sequence of ultrasound blood flow data frames and a sequence of ultrasound B-mode data frames of a region of interest including the vessel over a predetermined time period, wherein the region of interest comprises a longitudinal cross section of a length of the vessel and a landmark that is different than the vessel;
detecting, by the processor, a blood flow region indicating a blood flow along the length of the vessel in each frame of multiple frames in the sequence of ultrasound blood flow data frames and selecting a blood flow region among the detected blood flow regions based on a frame of the multiple frames in which the blood flow region is larger than a threshold;
segmenting, by the processor, the vessel in at least one frame of the sequence of ultrasound B-mode data frames based on the selected blood flow region, the at least one frame comprising the ultrasound B-mode data frame temporally corresponding to the ultrasound blood flow data frame in which the selected blood flow region is detected, wherein the segmenting comprises identifying an upper wall and a lower wall along the length of the vessel, and wherein the segmenting is based on seed points automatically derived from the selected blood flow region;
identifying, by the processor, the landmark in the at least one frame;
identifying, by the processor and based on the identified landmark, a longitudinal portion along the length of the vessel for deriving a feature;
deriving, by the processor at the identified longitudinal portion, a feature indicating a transverse size of the segmented vessel corresponding to a distance between the upper wall and the lower wall in each of the at least one frame; and
detecting a collapse of the vessel at a location of the vessel based on at least one of:
the distance between the upper wall and lower wall falling below a predetermined threshold at that location; or
a change in the distance between the upper wall and lower wall exceeding a predetermined threshold at that location.

14. The method of claim 13, wherein deriving the feature comprises deriving the feature at a first location in the vessel based on a second location of the identified landmark.

15. The method of claim 14, wherein the landmark comprises a hepatic vein, and identifying the landmark includes identifying the hepatic vein.

16. The method of claim 13, wherein controlling the ultrasound probe to simultaneously acquire the sequence of ultrasound blood flow frames and the sequence of ultrasound B-mode data frames comprises acquiring the at least one frame comprising the ultrasound B-mode data frame at a same time as the ultrasound blood flow data frame in which the selected blood flow region is detected.

17. A non-transitory computer-readable medium comprising computer program instructions which, when being executed, performs the method of claim 13.

\* \* \* \* \*